(12) United States Patent
Kim et al.

(10) Patent No.: US 6,995,361 B2
(45) Date of Patent: Feb. 7, 2006

(54) RADIAL DISK TYPE ION MOBILITY SPECTROMETER

(76) Inventors: Myung-jin Kim, A-dong, 2nd F-Da-Ho, Imun-row house, 2/1 293-2, Imun1-dong, Dongdaemun-gu, Seoul (KR) 130-826; Jae-yong Jeon, 636-15, Gojan2-dong, Ansan-si, Gyunggi-do (KR) 425-022

( * ) Notice: Subject to any disclaimer, the term of this patent is extended or adjusted under 35 U.S.C. 154(b) by 0 days.

(21) Appl. No.: 10/477,270

(22) PCT Filed: May 11, 2002

(86) PCT No.: PCT/KR02/00883

§ 371 (c)(1),
(2), (4) Date: Apr. 16, 2004

(87) PCT Pub. No.: WO03/005014

PCT Pub. Date: Jan. 16, 2003

(65) Prior Publication Data

US 2004/0173739 A1    Sep. 9, 2004

(30) Foreign Application Priority Data

May 11, 2001 (KR) ............................... 2001-25730

(51) Int. Cl.
*H01J 49/00* (2006.01)

(52) U.S. Cl. .................... 250/288; 250/287; 250/281; 324/464; 324/452

(58) Field of Classification Search ............... 250/287, 250/281; 324/464, 452
See application file for complete search history.

(56) References Cited

U.S. PATENT DOCUMENTS 4,712,008 A    12/1987 Vora et al.
(Continued)

FOREIGN PATENT DOCUMENTS

WO          88/05535       7/1998

*Primary Examiner*—Nikita Wells
*Assistant Examiner*—Zia R. Hashmi
(74) *Attorney, Agent, or Firm*—Volpe and Koenig, P.C.

(57) ABSTRACT

The present invention relates to a radial disk type ion mobility spectrometer, comprising: an ionizing chamber which is made of a cylindrical tube, and includes an inlet for supplying sample gas therethrough, an ionizing means for ionizing the supplied sample gas to generate ions having a predetermined polarity, and a slit formed by cutting away a part of a cylindrical wall corresponding to a predetermined width for discharging the ions therethrough; a shutter grid installed adjacent to the slit of the ionizing chamber for controlling passage of the ions through the slit; a drift chamber which is a hollow tube having a predetermined thickness and including an outer cylindrical wall having a predetermined diameter and an inner cylindrical wall having an inner diameter equal to an outer diameter to the ionizing chamber so that an annular space is formed between the inner and outer cylindrical walls, of which a part of the inner cylindrical wall corresponding to a width larger than that of the slit is cut away such that the ions passing through the slit can be introduced into the annular space through the cutaway part of the inner cylindrical wall, and of which the inner cylindrical wall is engaged with the cylindrical wall of the ionizing chamber in such a manner that the drift chamber communicates with the ionizing chamber through the slit and the cutaway part of the inner cylindrical wall; and a collector installed onto an inner surface of the outer cylindrical wall of the drift chamber for collecting the ions that have passed through the drift chamber.

10 Claims, 8 Drawing Sheets

U.S. PATENT DOCUMENTS

| | | | |
|---|---|---|---|
| 5,189,301 A * | 2/1993 | Thekkadath | 250/287 |
| 5,455,417 A | 10/1995 | Sacristan | |
| 5,621,208 A * | 4/1997 | Pourprix | 250/287 |
| 6,100,521 A | 8/2000 | Doring et al. | |
| 6,229,142 B1 | 5/2001 | Bateman et al. | |
| 6,727,496 B2 * | 4/2004 | Miller et al. | 250/287 |

* cited by examiner

RADIAL DISK TYPE ION MOBILITY SPECTROMETER

TECHNICAL FIELD

The present invention relates to a radial disk type ion mobility spectrometer, and more particularly, to a radial disk type ion mobility spectrometer which can improve the resolution and intensity of ion mobility remarkably by causing ion molecules to move in a radial direction far away from the center of a drift space having an annular section and to be collected into a collector mounted to an inner surface of an outer periphery of the annular drift space upon measurement of ion mobility.

BACKGROUND ART

An ion mobility spectrometer has been developed from the 1970 s in order to detect and analyze organic materials or pollutant materials in the air. By using the ion mobility spectrometer, the kind and the amount of a sample gas can be analyzed in a short time based on a peak current measured in the spectrometer and a moving speed of ions arriving at a collector.

The ion mobility spectrometer has been used to detect mines or components of chemical agents for the military purpose. Recently, it has been gradually applied widely in rummage for bearer of drugs or explosive materials, detection for gas leakage from industrial equipment, and the like.

The ion mobility spectrometer is divided into various types according to the structure of an ion reacting region for generating the ions and an ion moving region for making an electric field and causing the ions to move.

As a method of ionizing samples in the ion reacting region, there are the following two methods: a method of generating the ions using corona discharge or ultraviolet rays, and a method of ionizing the sample by using an ionization source such as radioactive isotope. Further, the structure of the ion moving region is generally classified into a conductively inlaid tube (CIT) structure, a stacked ring structure, and an ion lens structure.

FIG. 11 shows a schematic sectional view of a conventional cylinder type ion mobility analyzer, which comprises an analyzer housing 10, an ion moving tube 35 formed with an ion reacting region 15 and an ion moving region 30 installed within the housing 10, a shutter grid 25 installed within the ion moving region 30 of the ion moving tube 35, and an aperture grid 45 and a collector 40 installed within a rear end of the ion moving region 30 of the ion moving tube 35.

Further, a carrier gas source 20 and a sample gas source 30 are disposed at a front end of the housing 10 and a carrier gas and a sample gas supplied through the analyzer housing 10 to the ion reacting region 15, and a drift gas source 71 for supplying drift gas to the ion moving region 30 is connected at a rear end of the housing 10.

The shutter grid 25 is connected to an output terminal of a grid pulse generator 61 and to a timer circuit 60, and prevents the ions generated in the ion reacting region 15 from entering the ion moving region 30 until receipt of a driving pulse from the grid pulse generator. Further, the ion moving tube 35 is electrically connected with a high voltage supply 80 so that a uniform electric field can be generated within the ion moving tube 35.

The carrier gas injected into the ion reacting region 15 reacts with β particles, which are discharged from the ionization source 12 disposed in the ion reacting region 15, to generate positive and negative reactive ions, which react in turn with the sample gas to generate positive or negative product ions.

The reactive ions and the product ions are cut off by the shutter grid 25 while moving into a drift region, and then enter the ion moving region 30 at the moment the shutter grid 25 is opened, and finally move toward the collector 40.

At this time, the inert drift gas injected from the drift gas source 71 moves in a direction opposite to an ion moving direction while colliding with the ions, and is discharged through a drift gas discharge port 36. The ions introduced into the drift region are separated according to weight, size, charge, temperature, humidity, etc. while colliding with the drift gas, and reach the collector 40 at different speeds from one another. Thus, a predetermined current according to the sample gas is generated by the ions detected at the collector.

That is, the components of the sample are analyzed by a spectrum obtained from the current which is outputted from an amplifier 70 after being detected at the collector 40 based on the pulse inputted to the shutter grid 25 and amplified in the amplifier 70, and passing times of various kinds of ions passing through the ion moving region 30, which is measured by the timer circuit 60 connected to the grid pulse generator 61.

DISCLOSURE OF INVENTION

According to the aforementioned conventional cylinder type ion mobility analyzer, a plurality of aperture grids for causing the product ions to move parallel to the collector installed in the front of the shutter grid in a longitudinal axis of the analyzer are installed within the ion moving region. There are several problems in the aperture grids in that manufacturing processes thereof are complicated, the volume of the analyzer is increased, the intensity of the detected current is decreased since the ions are absorbed into the aperture grids on account of a high voltage applied thereto, and the resolution of the detected current is decreased since moving paths of the unabsorbed ions are lengthened.

Further, when the ions move parallel to the longitudinal direction within the ion moving region, energy of the ions are decreased and the moving paths of the ions deviate from the parallel path by mutual repulsive forces between the adjacent ions. Thus, the resolution and detection sensitivity are deteriorated.

Furthermore, there are problems in that since the conventional shutter grid is a slit or grid structure, the resolution is lowered if spacing of a slit or between grids is increased and signal sensitivity is lowered if the spacing of the slit or between the grids is not properly adjusted.

The present invention is conceived to solve the problems mentioned above. A first object of the present invention is to provide a radial disk type ion mobility spectrometer having an ion moving region, which can make ions to pass through a slit of a shutter grid and move toward a collector under a minimized influence exerted on the ions by mutual repulsive forces.

A second object of the present invention is to provide a radial disk type ion mobility spectrometer including an ion moving region and an ionizing chamber having a novel type of shutter grid instead of the conventional shutter grid.

A third object of the present invention is to provide a radial disk type ion mobility spectrometer wherein the structure thereof can be simplified and the size thereof can be reduced by installing a pair of simple ion path adjusting electrodes for performing a function of aperture grids within an ion moving region instead of a plurality of conventional aperture grids.

According to an aspect of the present invention for achieving the above objects, there is provided a radial disk type ion mobility spectrometer, comprising an ionizing chamber being a cylindrical hollow box, which is formed of an inlet for supplying sample gas therethrough, and a slit made by cutting away a part of a cylindrical wall corresponding to a predetermined width for discharging ionized ions therethrough, and including an ionizing means for ionizing the supplied sample gas to generate ions having a predetermined polarity; a shutter grid installed adjacent to the slit of the ionizing chamber for controlling passage of the ions through the slit; a drift chamber being a cylindrical hollow box including an outer cylindrical wall having a predetermined diameter and an inner cylindrical wall having an inner diameter equal to an outer diameter of the ionizing chamber so that an annular space is formed between the inner and outer cylindrical walls having a predetermined thickness, of which a part of the inner cylindrical wall corresponding to a width larger than that of the slit is cut away so that the ions passing through the slit can be introduced into the annular space through the cutaway part of the inner cylindrical wall, and of which the inner cylindrical wall is engaged with the cylindrical wall of the ionizing chamber in such a manner that the drift chamber communicates with the ionizing chamber through the slit and the cutaway part of the inner cylindrical wall; and a collector installed onto an inner surface of the outer cylindrical wall of the drift chamber for collecting the ions that have passed through the drift chamber.

Further, the shutter grid may be the cylindrical wall of the ionizing chamber in which the slit is formed.

Moreover, the ionizing means may be a corona discharge device.

Furthermore, in the present invention, a plurality of the corona discharge electrodes of the corona discharge device may be installed around the inlet to be symmetric with one another.

In addition, ion path adjusting electrodes in the form of an annular plate may be installed onto upper and lower surfaces within the drift chamber, respectively, to be symmetric with and parallel to each other at a predetermined distance around a concentric central axis of the ion mobility spectrometer.

Also, uneven parts may be formed onto opposite faces of the ion path adjusting electrodes.

The uneven parts of the ion path adjusting electrodes may take the shape of annular saw teeth each of which has a vertical surface upstream of an ion flow and an inclined surface downstream of the ion flow.

Further, in the present invention, a plurality of supply ports for supplying drift gas into the drift chamber may be formed onto the outer cylindrical wall of the drift chamber, and a plurality of discharge ports for discharging the drift gas to the outside of the drift chamber are formed at a top or bottom surface of the drift chamber between the shutter grids and radially inner ends of the annular ion path adjusting electrodes.

Moreover, each of the plurality of supply ports and the plurality of discharge ports are disposed onto an identical circumference to be symmetric with one another.

Furthermore, in the present invention, cutaway surfaces defining the slit of the ionizing chamber are formed to slantingly face the drift chamber.

BEST MODE FOR CARRYING OUT THE INVENTION

Hereinafter, preferred embodiments of the present invention will be explained in detail with reference to the accompanying drawings.

Figure 1:
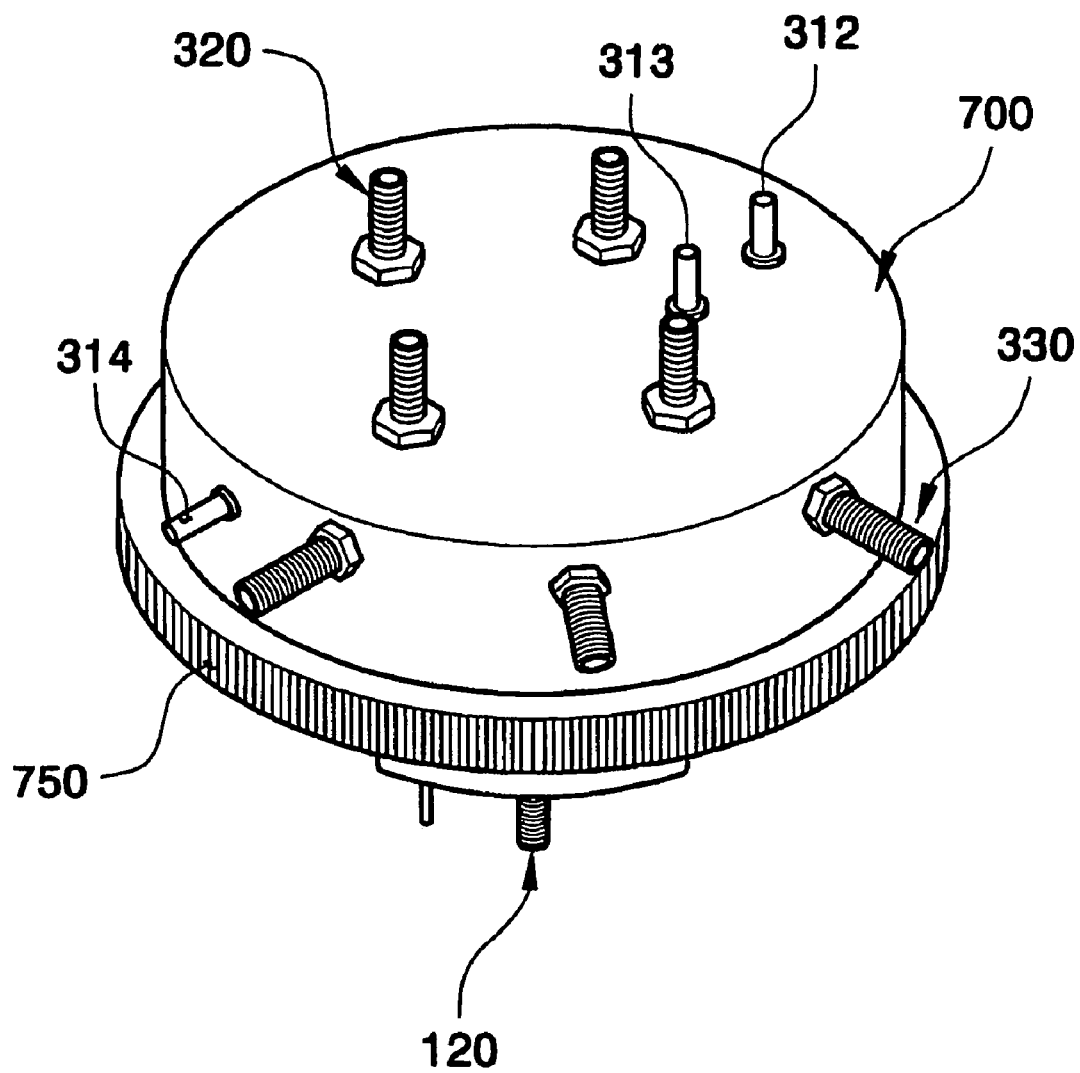
FIG. 1 is a perspective view of a radial disk type ion mobility spectrometer according to an embodiment of the present invention.
Figure 2:
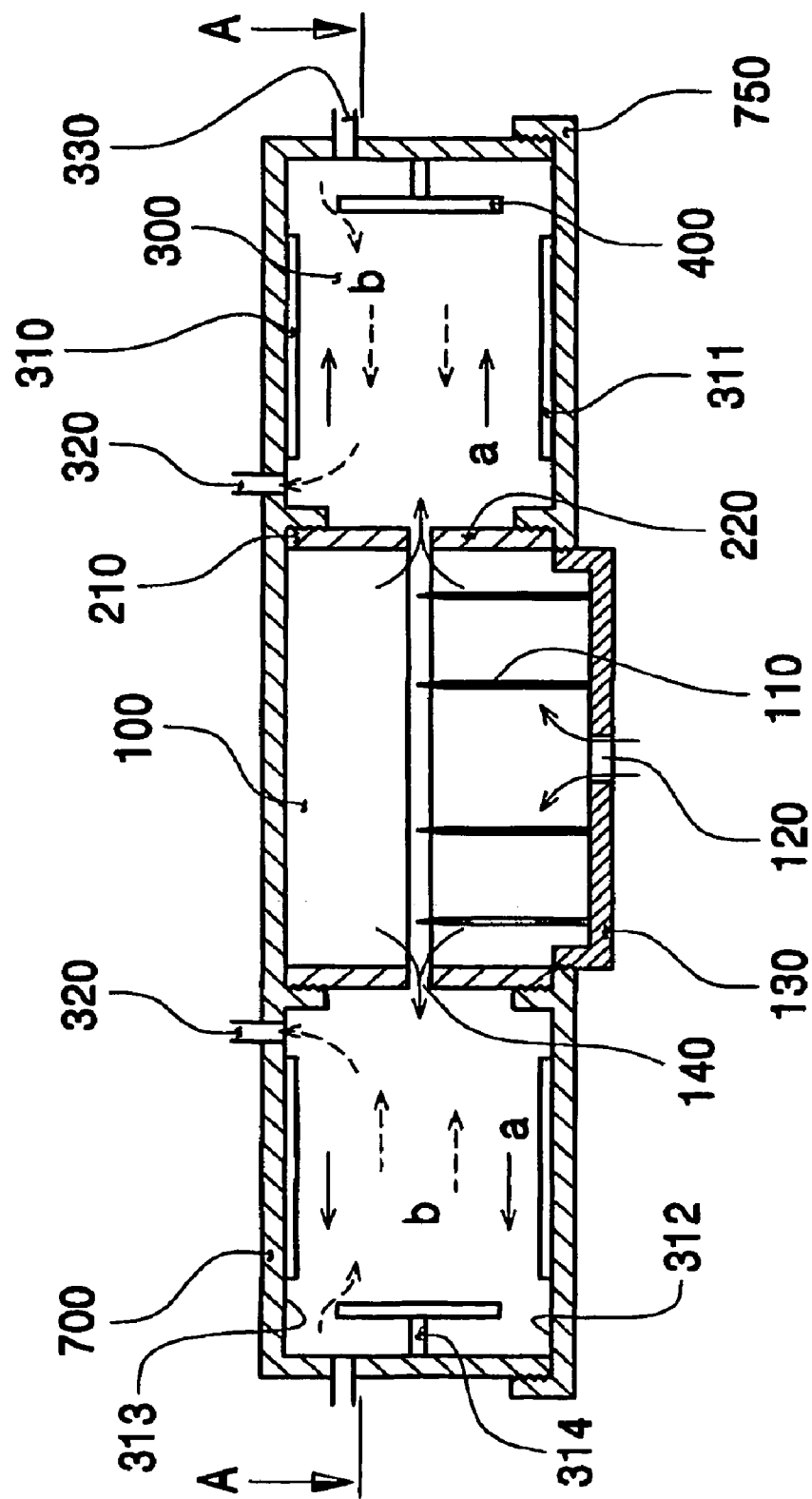
FIG. 2 is a schematic sectional view of the radial disk type ion mobility spectrometer according to the embodiment of the present invention.

FIG. 1 is a perspective view of a radial disk type ion mobility spectrometer according to a preferred embodiment of the present invention, and FIG. 2 is a schematic sectional view of the radial disk type ion mobility spectrometer according to the embodiment of the present invention.

As shown in FIG. 1, the ion mobility spectrometer of the present invention has a disk type slim external appearance in which ions move in a radial direction. The spectrometer is provided with an inlet 120 for supplying samples at the center of a bottom surface thereof, supply ports 330 for supplying drift gas at a circumferential surface thereof, and discharge ports 320 for discharging the drift gas at a top surface thereof. Reference numeral 312 designates a terminal for supplying electric power to ion path adjusting electrodes 310, reference numeral 313 designates a terminal for supplying electric signals to a shutter grid 210, and reference numeral 314 designates a terminal for outputting electric signals generated from a collector 400.

As shown in FIG. 2, the spectrometer of the present invention comprises an ionizing chamber 100 for ionizing the samples, shutter grids 210, 220 for allowing and preventing movement of the ions into a drift chamber, the drift chamber 300 for providing a path along which the ions passed through the shutter grids move toward a collector, and the collector 400 installed within the drift chamber for collecting the ions and thus generating electrical signals.

The ionizing chamber 100 is a cylindrical hollow box. The inlet 120 through which sample gas is supplied is formed at the center of the bottom surface thereof, and a slit 140 formed by removing a portion corresponding to a predetermined width from an outer periphery of the chamber is formed on the outer periphery so that the ionized ions can be discharged through the slit. Further, a plurality of corona discharge electrodes 110 for ionizing the supplied sample gas to have a predetermined polarity are installed around the inlet 120 in an angularly symmetrical manner. It is preferred that the width of the slit be smaller than thickness of the ionizing chamber 100. In general, the width of the slit is within a range of 0.5 to 1 mm.

A general shutter grid may be installed in the front of the slit, but the present invention has proposed a novel structure that can substitute for the shutter grid in view of its function. That is, according to the present invention, a cylindrical wall serving as a component of the ionizing chamber 100 performs the function of the shutter grid. The cylindrical wall of the ionizing chamber is cut into two parts at the center thereof to form the slit threrbetween, and it is separated into the upper and lower shutter grids 210, 220. An electric field generated in slit spacing is controlled by adjusting electrical signals applied to the upper and lower shutter grids so that the movement of the ions into the drift chamber can be prevented or permitted. Therefore, the cylindrical wall of the ionizing chamber, in which the slit has been formed, also serves as the shutter grid.

The drift chamber 300 is a cylindrical hollow box having a predetermined thickness, which includes an outer cylindrical wall having a predetermined diameter and an inner cylindrical wall having an inner diameter equal to an outer diameter of the ionizing chamber and in which an annular space is formed between the inner and outer cylindrical walls. Further, a part of the inner cylindrical wall corresponding to a width larger than that of the slit is cut away such that the ions passing through the slit 140 can be introduced into the annular space through the cutaway part of the inner cylindrical wall. In addition, the inner cylindrical wall of the drift chamber 300 is engaged with the outer periphery of the ionizing chamber in such a manner that the drift chamber communicates with the ionizing chamber through the slit and the cutaway part of the inner cylindrical wall.

Ion path adjusting electrodes 310, 311 in the form of an annular plate are also installed onto upper and lower surfaces 313, 312 within the drift chamber 300, respectively. In particular, the ion path adjusting electrodes are installed to be symmetric with and parallel to each other at a predetermined distance around a concentric central axis of the ion mobility spectrometer. The ion path adjusting electrodes may be installed onto the upper and lower surfaces in such a manner that they are constructed by a plurality of divided annular plates. In a case where an ion path intends to be controlled after installing the ion path adjusting electrodes, the conventional ion mobility analyzer should control two degrees of freedom, but control of only the movement in a vertical axis (Z-axis) is sufficient for the ion mobility spectrometer of the present invention because the structure of the drift chamber is formed to be expanded in the radial direction. Thus, the degree of freedom to be controlled becomes one.

The collector 400 is installed around an inner circumferential surface of the outer cylindrical wall of the drift chamber 300 to collect the ions passing through the drift chamber. That is, the collector 400 takes the shape of a hoop. In particular, the collector is preferably installed to be spaced apart at a predetermined distance from the outer cylindrical wall of the drift chamber so that the former can be isolated from the latter.

In addition, a plurality of supply ports 330 for supplying the drift gas into the drift chamber is formed on the outer cylindrical wall of the chamber, and a plurality of discharge ports 320 for discharging the drift gas to the outside are formed on the top surface of the chamber. It is preferred that the supply ports 330 be formed on the outer cylindrical wall of the drift chamber to be symmetric with one another and the discharge ports be formed on a predetermined concentric circle to be symmetric with one another.

Figure 3:
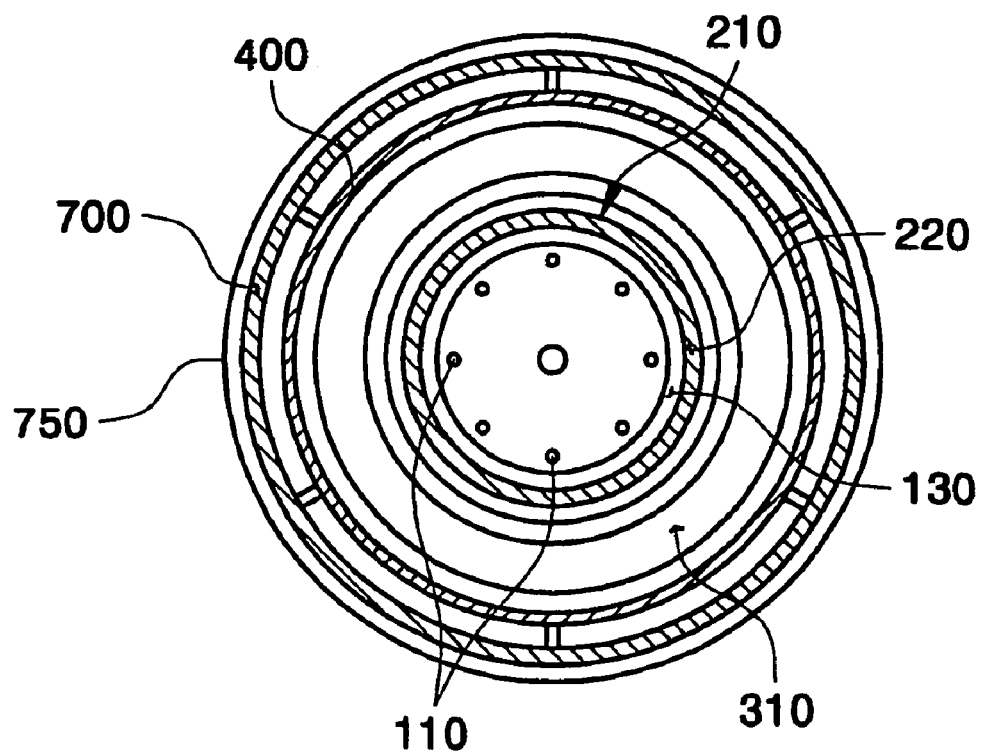
FIG. 3 is a sectional view taken along line A—A of FIG. 2.

FIG. 3 is a sectional view taken along line A—A of FIG. 2, and shows that corona discharge electrodes 110 are formed to be symmetric with one another and that the hoop shaped collector 400 is installed to be spaced apart from the outer cylindrical wall of the drift chamber at a predetermined distance.

Figure 4:
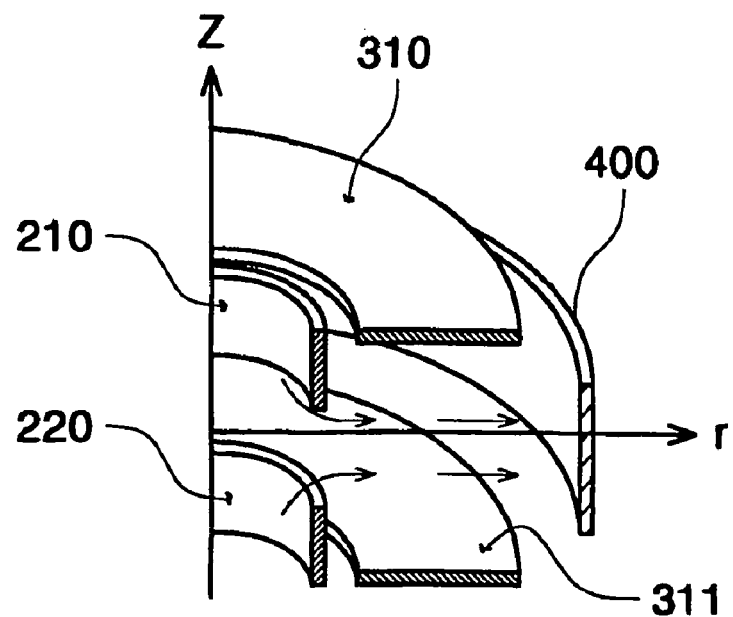
FIG. 4 is a view illustrating an ion flow within the ion mobility spectrometer according to the embodiment of the present invention.

FIG. 4 is a view illustrating an ion flow within the ion mobility spectrometer according to the embodiment of the present invention. In the figure, there is shown, by using arrows, a state where the ionized samples move from the ionizing chamber through both the shutter grids and the drift chamber and are collected onto the collector. At this time, since the ions move into the space that is expanded in the radial direction, they are little influenced by a space charge effect due to the mutual repulsive forces thereof. Thus, straight movement of the ions can be maximized without any path deviation thereof. Accordingly, it can be understood that the resolution and signal intensity can be improved.

Figure 5:
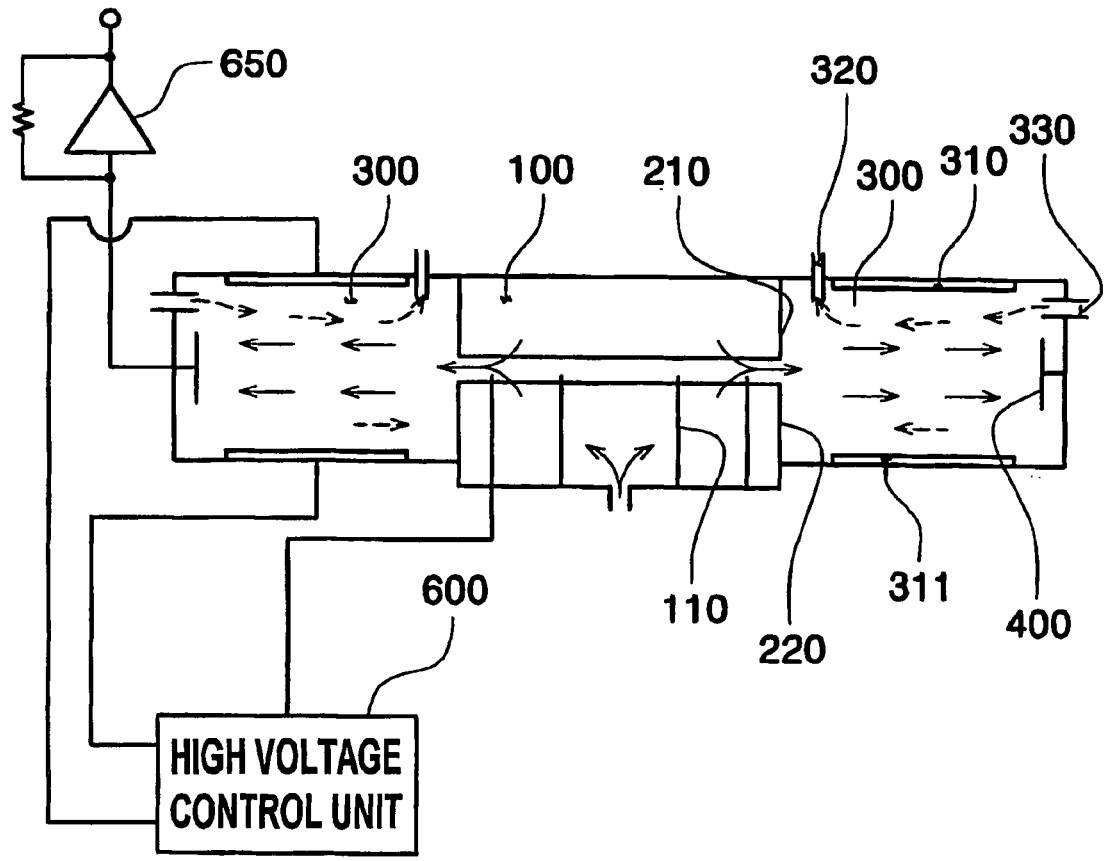
FIG. 5 is a schematic view illustrating an overall flow of ions and gas within the ion mobility spectrometer according to the embodiment of the present invention.

FIG. 5 is a schematic view illustrating an overall flow of the ions and gas within the ion mobility spectrometer according to the embodiment of the present invention. In the figure, the movement of the ions is denoted as solid arrows whereas movement of the drift gas is denoted as dashed arrows. The samples supplied into the ionizing chamber 100 are ionized when a control unit 600 causes electric voltage to be applied to the corona discharge electrodes, and the generated ions can be supplied into the drift chamber by applying the electric signals to the shutter grids. Since the drift gas suppresses mutual interaction between the ions supplied into the drift chamber, a large amount of the ions can reach the collector. The drift gas supplied into the drift chamber flows in a direction counter to the flow direction, and is then discharged to the outside through the discharge ports 320 adjacent to the shutter grids.

Figure 6:
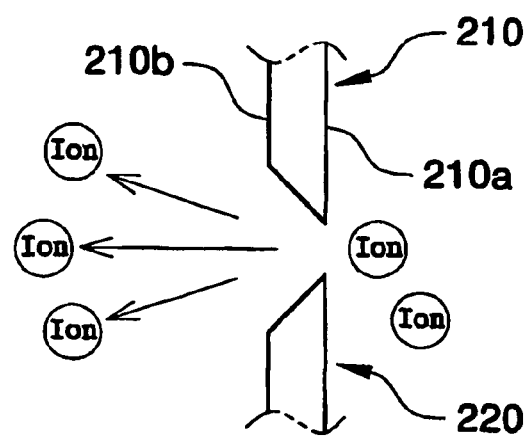
FIG. 6 is a view illustrating a shape of shutter grids according to another embodiment of the present invention.

FIG. 6 is a view illustrating a shape of the shutter grids according to another embodiment of the present invention. In the figure, there is shown a structure of the cylindrical wall of the ionizing chamber serving as the shutter grids, by which loss of the ions produced when the ions pass through the cylindrical wall of the ionizing chamber can be minimized. That is, the structure is to reduce an influence of ion scattering produced when the ions collide against the cylindrical wall.

Figure 7:
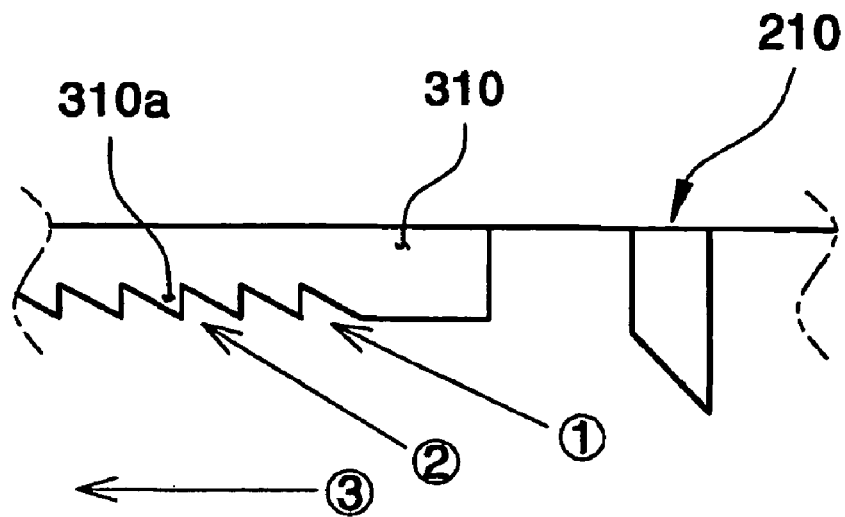
FIG. 7 is a view illustrating a concavo-convex shape of ion path adjusting electrodes according to the embodiment of the present invention.

FIG. 7 is a view illustrating an uneven or concavo-convex shape of ion path adjusting electrodes according to the embodiment of the present invention. In the figure, there is shown a structure of the ion path adjusting electrodes with uneven parts 310a formed thereon for reducing an influence of ion scattering produced when the ions collide against the ion path adjusting electrodes. In particular, the uneven parts are preferably constructed such that vertical surfaces thereof are upstream of the ion flow and inclined surfaces thereof are downstream of the ion flow. The uneven parts formed on the ion path adjusting electrodes take the shape of annular grooves.

Figure 8:
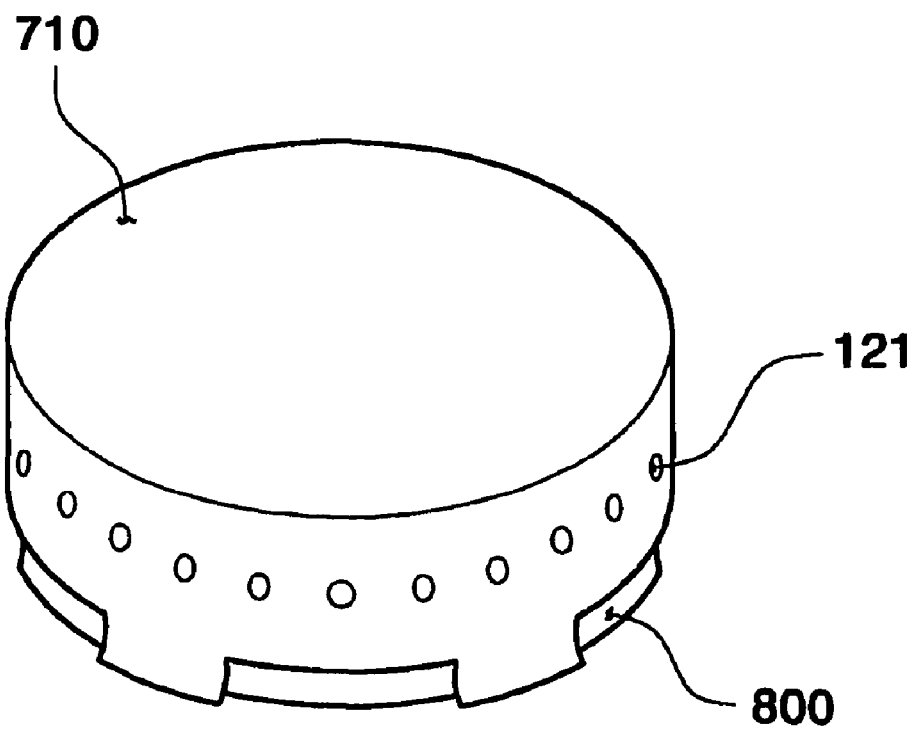
FIG. 8 is a perspective view illustrating a state where the ion mobility spectrometer according to an embodiment of the present invention is employed in a gas mask.
Figure 9:
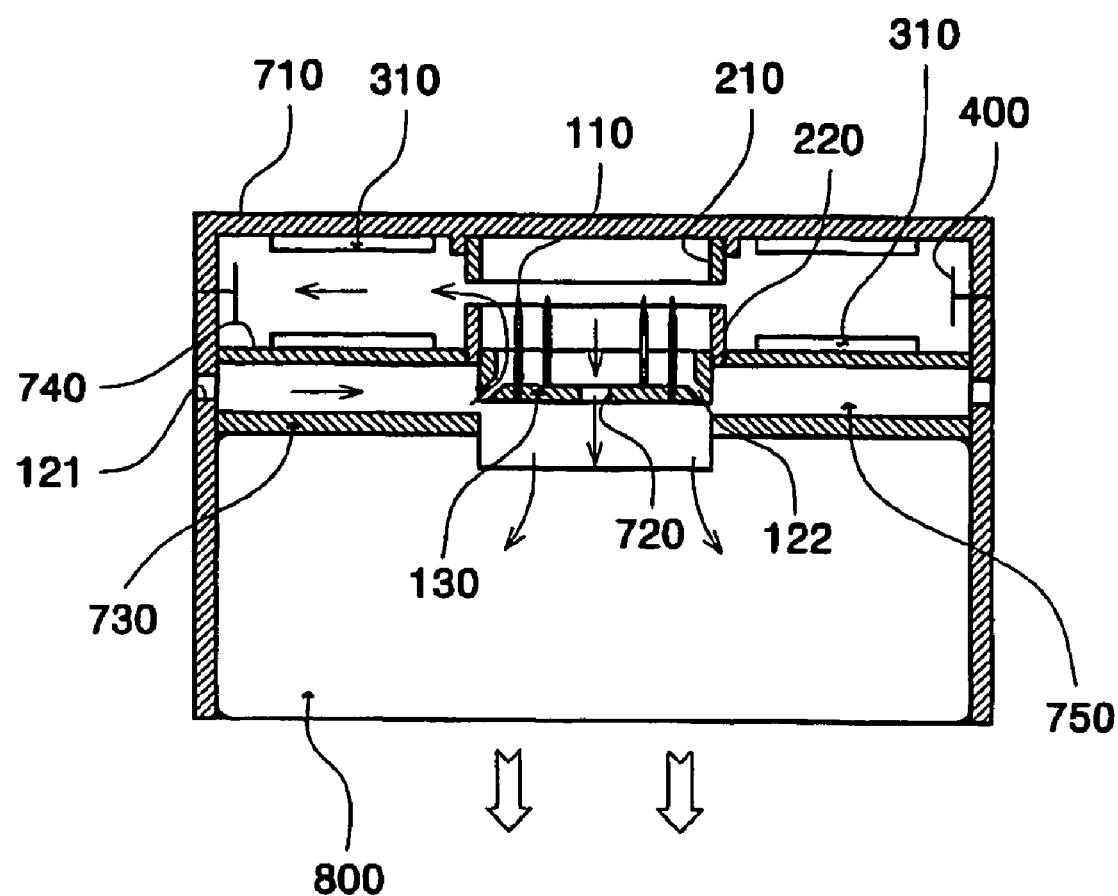
FIG. 9 is a schematic sectional view of the gas mask shown in FIG. 8.
Figure 10:
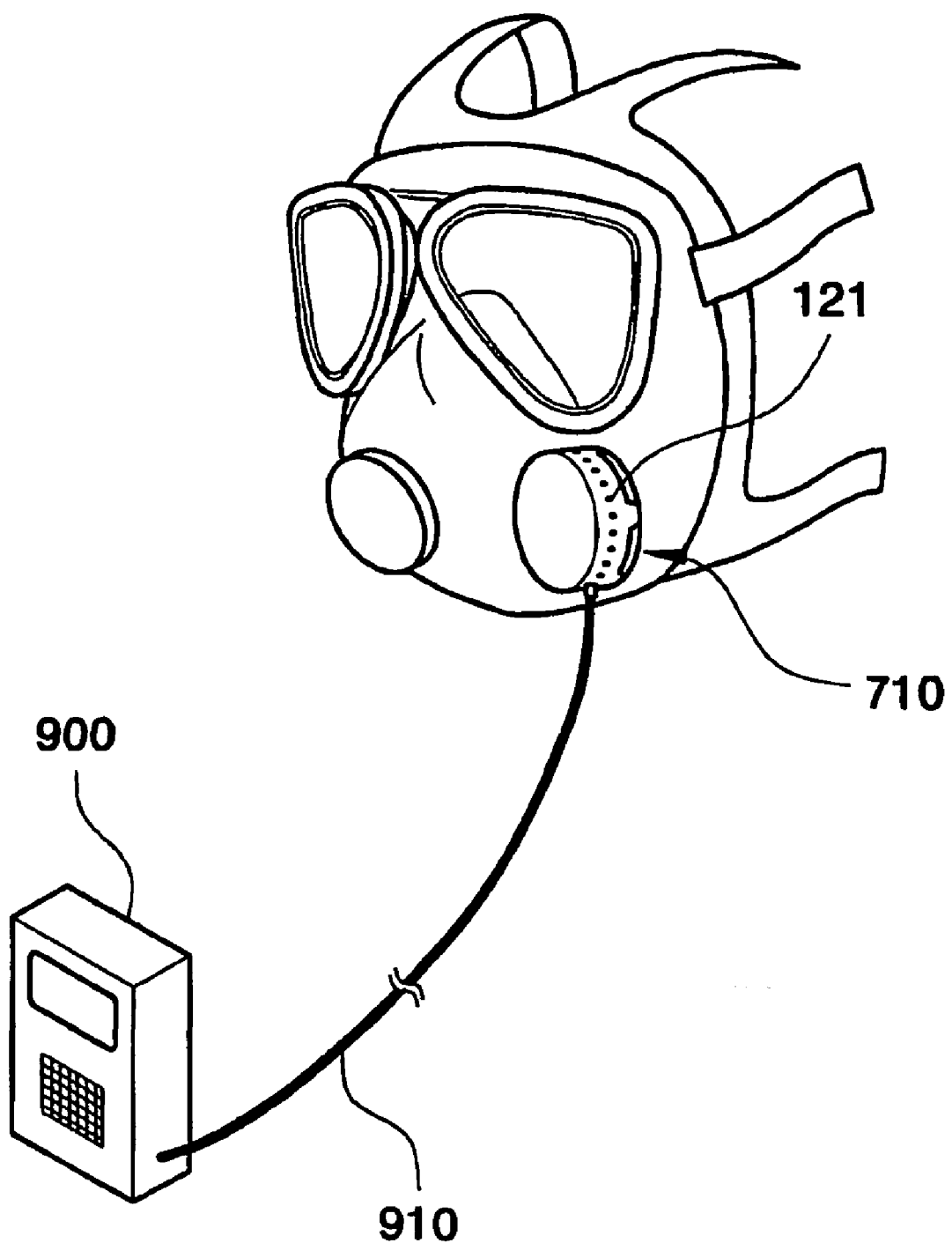
FIG. 10 is a view showing a state where the ion mobility spectrometer according to the present invention is applied to and used in the gas mask.
Figure 11:
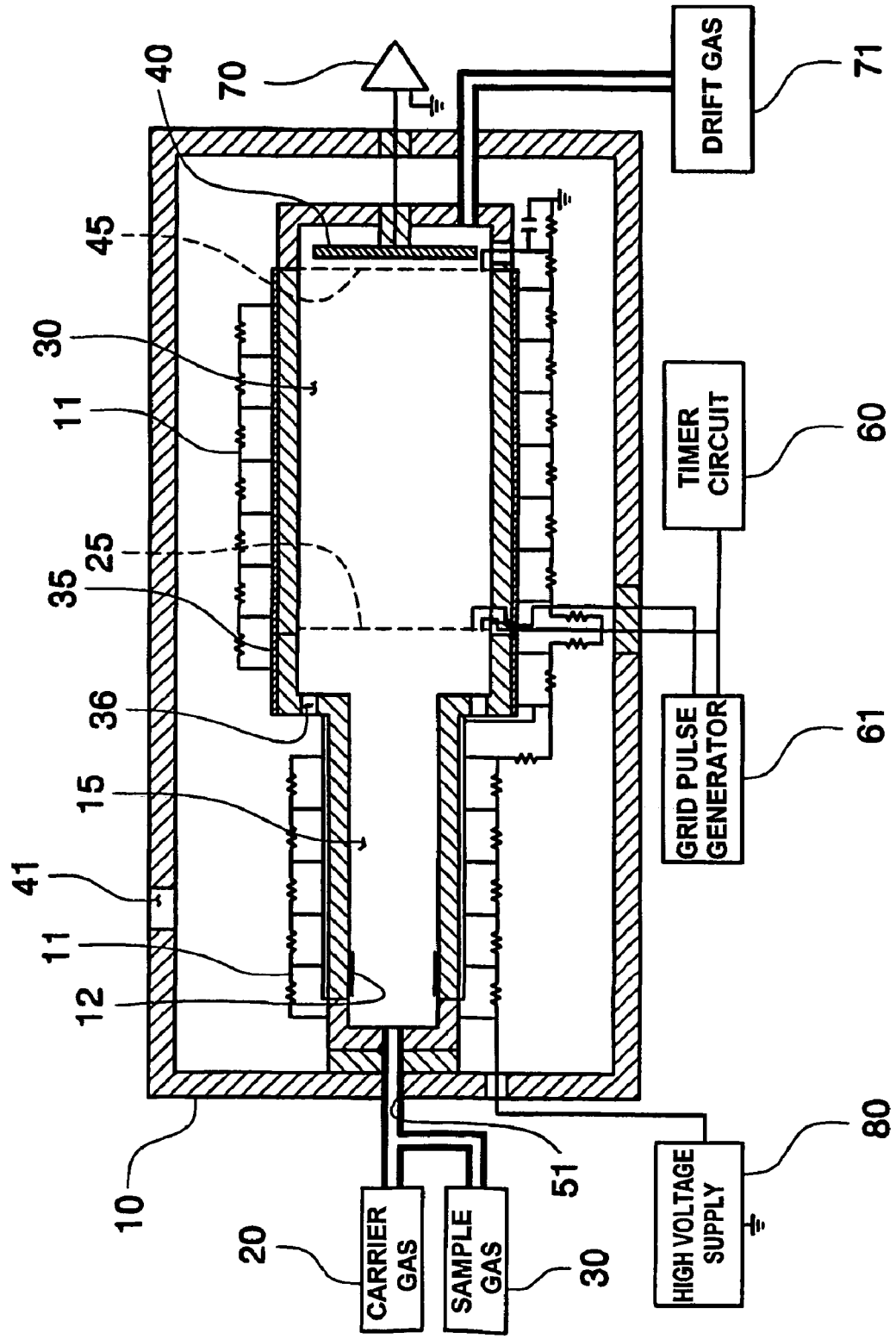
FIG. 11 is a schematic sectional view of a conventional cylinder type ion mobility analyzer.

FIG. 8 is a perspective view showing a state where the ion mobility spectrometer according to an embodiment of the present invention is employed in a gas mask. FIG. 9 is a schematic sectional view of the gas mask shown in FIG. 8. Since the ion mobility spectrometer of the present invention is slim and compact, it can be easily installed to and utilized in the gas mask and the like. In such a case, as shown in FIG. 9, the drift chamber may not include the holes for supplying and/or discharging the drift gas into and/or from the drift chamber. FIG. 10 shows a state where the gas mask with the ion mobility spectrometer of the present invention attached thereto is connected to and utilized together with a measuring instrument. It is understood from the figure that since the measuring instrument is also compact, a person wearing the gas mask can freely move while holding the measuring instrument to his/her body.

INDUSTRIAL APPLICABILITY

As described above, since the ion moving region expanded in the radial direction is provided in the ion mobility spectrometer of the present invention, the influence on the ion path exerted by the mutual repulsive forces of the ions moving toward the collector through the slit of the shutter grids can be minimized. Thus, the resolution and the signal intensity can be improved.

Further, according to the ion mobility spectrometer of the present invention, since a new type of shutter grid capable of causing the ions to move along the straight ion path substitutes for the conventional shutter grid, detection efficiency of the spectrometer can be improved and the structure thereof can also be simplified.

Furthermore, according to the ion mobility spectrometer of the present invention, since the degree of freedom required for controlling the ion movement is reduced from two to one, a pair of ion path adjusting electrodes capable of performing a function of the aperture grids can be utilized instead of a plurality of the conventional aperture grids. Thus, the structure of the spectrometer can be simplified and electrical control thereof can also be easily performed.

It should be understood that the embodiments of the present invention as described above and illustrated in the figures are not construed as limiting the technical spirit of the present invention. The scope of the invention is defined only by the appended claims, and those skilled in the art can make various changes and modifications to the embodiments of the present invention within the scope of the invention. Thus, such changes and modifications fall within the scope of the invention as far as they are obvious to those skilled in the art.

What is claimed is:

1. A radial disk type ion mobility spectrometer, comprising:
    an ionizing chamber being a cylindrical hollow box, which is formed of an inlet for supplying sample gas therethrough, and a slit made by cutting away a part of a cylindrical wall corresponding to a predetermined width for discharging ionized ions therethrough, and including an ionizing means for ionizing the supplied sample gas to generate ions having a predetermined polarity;
    a shutter grid installed adjacent to the slit of the ionizing chamber for controlling passage of the ions through the slit;
    a drift chamber being a cylindrical hollow box including an outer cylindrical wall having a predetermined diameter and an inner cylindrical wall having an inner diameter equal to an outer diameter of the ionizing chamber so that an annular space is formed between the inner and outer cylindrical walls having a predetermined thickness, of which a part of the inner cylindrical wall corresponding to a width larger than that of the slit is cut away so that the ions passing through the slit can be introduced into the annular space through the cutaway part of the inner cylindrical wall, and of which the inner cylindrical wall is engaged with the cylindrical wall of the ionizing chamber in such a manner that the drift chamber communicates with the ionizing chamber through the slit and the cutaway part of the inner cylindrical wall; and
    a collector installed onto an inner surface of the outer cylindrical wall of the drift chamber for collecting the ions that have passed through the drift chamber, wherein the slit of the ionizing chamber and the collector being placed on the same line of the radial direction of the drift chamber.

2. The radial disk type ion mobility spectrometer as claimed in claim 1, wherein the shutter grid is the cylindrical wall of the ionizing chamber in which the slit is formed.

3. The radial disk type ion mobility spectrometer as claimed in claim 1, wherein the ionizing means is a corona discharge device.

4. The radial disk type ion mobility spectrometer as claimed in claim 3, wherein a plurality of the corona discharge electrodes of the corona discharge device are installed around the inlet to be symmetric with one another.

5. The radial disk type ion mobility spectrometer as claimed in claim 1, further comprising ion path adjusting electrodes in the form of an annular plate installed onto upper and lower surfaces within the drift chamber, respectively, to be symmetric with and parallel to each other at a predetermined distance around a concentric central axis of the ion mobility spectrometer.

6. The radial disk type ion mobility spectrometer as claimed in claim 5, wherein uneven parts are formed onto opposite faces of the ion path adjusting electrodes.

7. The radial disk type ion mobility spectrometer as claimed in claim 6, wherein the uneven parts of the ion path adjusting electrodes take the shape of annular saw teeth each of which has a vertical surface upstream of an ion flow and an inclined surface downstream of the ion flow.

8. The radial disk type ion mobility spectrometer as claimed in claim 1, wherein a plurality of supply ports for supplying drift gas into the drift chamber are formed onto the outer cylindrical wall of the drift chamber, and a plurality of discharge ports for discharging the drift gas to the outside of the drift chamber are formed at a top or bottom surface of the drift chamber between the shutter grids and radially inner ends of the annular ion path adjusting electrodes.

9. The radial disk type ion mobility spectrometer as claimed in claim 8, wherein each of the plurality of supply ports and the plurality of discharge ports are disposed onto an identical circumference to be symmetric with one another.

10. The radial disk type ion mobility spectrometer as claimed in claim 2, wherein cutaway surfaces defining the slit of the ionizing chamber are formed to slantingly face the drift chamber.

* * * * *